United States Patent
Chouippe et al.

(10) Patent No.: US 8,592,601 B2
(45) Date of Patent: Nov. 26, 2013

(54) PRECURSOR PHASE AND USE THEREOF FOR PREPARING THE MAGNESIUM TETRAHYDRATE SALT OF AN OMEPRAZOLE ENANTIOMER

(75) Inventors: Snella Chouippe, Charpont (FR); Jean-Marie Schneider, Magnanville (FR); Guillaume Tauvel, Rouen (FR); Gerard Coquerel, Mont Saint Aignan (FR)

(73) Assignees: Produits Chimiques Auxiliaires et de Synthese, Longjumeau (FR); Universite de Rouen, Mount-Saint-Aignan (FR)

( * ) Notice: Subject to any disclaimer, the term of this patent is extended or adjusted under 35 U.S.C. 154(b) by 197 days.

(21) Appl. No.: 13/076,989

(22) Filed: Mar. 31, 2011

(65) Prior Publication Data

US 2011/0269798 A1   Nov. 3, 2011

Related U.S. Application Data

(60) Provisional application No. 61/423,720, filed on Dec. 16, 2010.

(30) Foreign Application Priority Data

May 3, 2010   (FR) ...................... 10 53419

(51) Int. Cl.
*C07D 401/12*   (2006.01)

(52) U.S. Cl.
USPC ..................................... 546/273.7

(58) Field of Classification Search
USPC ..................................... 546/273.7
See application file for complete search history.

(56) References Cited

U.S. PATENT DOCUMENTS

2009/0124811 A1   5/2009   Coquerel et al.

FOREIGN PATENT DOCUMENTS

| FR | 2 920 428 A1 | 3/2009 |
|---|---|---|
| WO | 96/01623 A1 | 1/1996 |
| WO | 98/54171 A1 | 12/1998 |
| WO | 01/14367 A1 | 3/2001 |
| WO | 2004/002982 A2 | 1/2004 |
| WO | 2004/046134 A2 | 6/2004 |
| WO | 2004/089935 A1 | 10/2004 |
| WO | 2006/096709 A2 | 9/2006 |
| WO | 2007/031845 A2 | 3/2007 |
| WO | 2008/102145 A2 | 8/2008 |
| WO | 2009/027614 A2 | 3/2009 |

OTHER PUBLICATIONS

French Search Report, dated Jan. 21, 2011, from corresponding French application.

*Primary Examiner* — Patricia L Morris
(74) *Attorney, Agent, or Firm* — Young & Thompson (57) ABSTRACT

A precursor phase of the magnesium tetrahydrate salt of an omeprazole enantiomer, and also processes for preparing it and its use for the preparation of the magnesium tetrahydrate salt are described. Crystals of the magnesium tetrahydrate salt thus obtained, and their uses, especially in the synthesis of the dihydrate form A of the magnesium salt of the enantiomer or as medicament are also disclosed.

13 Claims, 6 Drawing Sheets

FIGURE 1: Diffractogram of the magnesium salt of amorphous (S) omeprazole

TGA-DSC of the magnesium salt of (S) omeprazole tetrahydrate

PRECURSOR PHASE AND USE THEREOF FOR PREPARING THE MAGNESIUM TETRAHYDRATE SALT OF AN OMEPRAZOLE ENANTIOMER

FIELD OF THE INVENTION

The present invention relates to a precursor phase of the magnesium tetrahydrate salt of an omeprazole enantiomer, and also to processes for preparing it and to its use for the preparation of said magnesium tetrahydrate salt. The invention also relates to crystals of the magnesium tetrahydrate salt thus obtained, and to their use, especially in the preparation of the dihydrate form A of the magnesium salt of said enantiomer.

BACKGROUND OF THE INVENTION

Alkali metal and alkaline-earth metal salts of omeprazole and enantiomers thereof are well known as gastric secretion inhibitors and antiulcer agents. Among these, the magnesium salt of the (S) enantiomer of omeprazole, or esomeprazole or 5-methoxy-2-[(S)-[4-methoxy-3,5-dimethyl-2-pyridinyl) methyl]sulfinyl]-1H-benzimidazole, is the first proton pump inhibitor (PPI) developed and sold in pure enantiomer form. The company Astra Zeneca thus markets this compound in trihydrate form, under the trade name Inexium®. Other companies have developed a magnesium salt of esomeprazole in dihydrate form.

Processes for preparing these compounds are described in the literature.

Thus, patent application WO 2004/002982 describes the separation of racemic omeprazole into its pure enantiomers by formation of diastereomeric salts from the sodium salt of racemic omeprazole placed in contact with the coordinating agent diethyl-D-tartrate/Ti (iso-Pr)$_4$ in acetone and complexation using L-mandelic acid. Selective crystallization of the diastereomer comprising esomeprazole followed by a basic hydrolysis gives the magnesium salt of esomeprazole trihydrate in 99% ee. Formation of the corresponding dihydrate is obtained by controlled drying.

Patent application WO 2004/046134 describes the preparation of the magnesium salt of esomeprazole trihydrate in crystalline form II from the amorphous form of the same salt, which is dissolved in methanol to form a solution. After filtration, removal of the solvent and precipitation from water, a solid is obtained, which is washed with a mixture of water and acetone and then dried.

Patent application WO 2004/089935 also describes the preparation of a novel crystalline form of the magnesium salt of esomeprazole trihydrate, known as H1, characterized by its powder X-ray diffraction diagram.

Patent application WO 2007/031845 also describes the preparation of a magnesium salt of esomeprazole trihydrate, in two polymorphic crystalline forms G1 and G2, by reacting the sodium salt of esomeprazole with aqueous magnesium sulfate solution.

For its part, patent application WO 98/54171 describes the formation of the magnesium salt of the omeprazole trihydrate enantiomers, and also of the dihydrate in the crystalline forms A and B. It is indicated that the trihydrate of the magnesium salt of esomeprazole may be prepared by hydration of a magnesium salt of esomeprazole of crystalline form I, obtained as described in document WO 96/01623, i.e. from esomeprazole and magnesium methoxide in acetone. As a variant, the trihydrate may be prepared by reacting the potassium salt of esomeprazole with magnesium sulfate in water. To obtain the dihydrate form A, magnesium sulfate is dissolved in methanol, and a mixture of water and acetone is then added to the reaction product.

Document WO 2008/102145 teaches an alternative process for the crystallization of the dihydrate form A, which is supposed to overcome the insufficiencies of the process described in WO 98/54171, which is said to lead to an unstable compound, which is liable to become converted on drying into trihydrate or into an amorphous form. Examples to 9 of WO 2008/102 145 thus disclose a process comprising steps of: (a) reacting the potassium salt of esomeprazole with a magnesium salt (such as magnesium chloride hexahydrate) in alcoholic medium (especially in methanol), (b) filtration of the insoluble matter, (c) addition of a water/acetone mixture to the insoluble matter, (d) filtration, washing with ethyl acetate and drying.

Such a process requires the use of several organic solvents, some of which, such as methanol, may pose toxicology problems, and which must in any case be removed during the process in order to obtain a product that is as pure as possible.

More recently, patent application FR 2 920 428 has proposed a process described as leading to the magnesium salt of esomeprazole tetrahydrate. This process, illustrated in Example 10 of said application, consists in dissolving in aqueous potassium hydroxide solution a potassium salt of esomeprazole, and then in reacting this salt with magnesium chloride dissolved in a mixture of water and acetone. It is indicated that the tetrahydrate is obtained in an unoptimized yield of 35%. The inventors however realized, after numerous attempts, that this process was not reproducible and led almost every time to the trihydrate of the magnesium salt of esomeprazole.

The general description of said document suggests other processes for synthesizing the tetrahydrate by cation exchange starting with the potassium salt, without further details. Now, the teaching of the prior art mentioned previously shows that the reaction of a magnesium salt with the same potassium salt of esomeprazole, as a function especially of the solvents used, leads to a diversity of crystalline and/or hydrate forms. In addition, the need to perform the reaction in the presence of potassium hydroxide induces pollution of the product obtained with residual potassium ions, which affects the purity of this product.

It would thus be desirable to have available a novel process for preparing a magnesium salt of an enantiomer of omeprazole tetrahydrate that is economical, easy to perform, and that leads reproducibly and in a yield of at least 50% to a compound whose purity is acceptable for pharmaceutical use, especially with a low content of potassium.

SUMMARY OF THE INVENTION

In this context, the inventors have developed a process for preparing the magnesium salt of (S) omeprazole tetrahydrate that satisfies this need. This process may be readily transposed to the preparation of the corresponding diastereomer. In an entirely surprising manner, such a process leads reproducibly to the tetrahydrate of this salt, whereas acetone is rather known for its dehydrating effect, and as such it would have been expected to obtain the trihydrate, or even the dihydrate of this salt.

The inventors have moreover demonstrated the formation, in this preparation process, of a precursor phase of the magnesium tetrahydrate salt of the enantiomer, which conditions the production of this tetrahydrate and has never been demonstrated before, to the inventors' knowledge.

One subject of the present invention is thus a precursor phase of the magnesium tetrahydrate salt of an omeprazole enantiomer (referred to hereinbelow as the "precursor phase"), characterized in that its X-ray diffractogram has the following characteristic peaks:

| d (Ångströms) | 2-Theta (°) | Relative intensity (%) |
|---|---|---|
| 19.80 | 4.45 | very strong |
| 12.17 | 7.25 | weak |
| 10.78 | 8.19 | medium |
| 9.26 | 9.53 | weak |
| 7.28 | 12.14 | weak |
| 6.79 | 13.03 | weak |
| 5.22 | 16.95 | weak |
| 5.01 | 17.67 | medium |
| 4.821 | 18.38 | weak |
| 4.009 | 22.15 | weak |

A subject of the invention is also three processes for preparing said precursor phase.

The first of these processes comprises the reslurrying of a magnesium salt of said enantiomer in amorphous form, in a solvent/water mixture, said solvent being chosen from water-miscible nonalcoholic organic solvents and the volume ratio of the solvent to water being between 95/5 and 30/70.

The second process comprises:
the dissolution of an optionally solvated alkali metal salt of said omeprazole enantiomer in a solvent/water mixture, said solvent being chosen from water-miscible nonalcoholic organic solvents and the volume ratio of the solvent to water being between 90/10 and 50/50,
the mixing of said solution of alkali metal salt with an aqueous solution of a magnesium salt free of organic solvent, to form a suspension.

The third process comprises:
the reslurrying in at least one water-miscible nonalcoholic organic solvent, to the exclusion of any other solvent, of a magnesium salt of the amorphous or crystalline, optionally hydrated or solvated omeprazole enantiomer,
the addition of water to the product thus obtained.

A subject of the present invention is also a process for preparing a magnesium tetrahydrate salt of an omeprazole enantiomer, comprising the filtration and then drying of a suspension containing the abovementioned precursor phase, or obtained according to one of the processes described above.

The invention also relates to crystals of the magnesium tetrahydrate salt of an omeprazole enantiomer, which may be obtained according to this process.

A subject of the invention is moreover these crystals for use as medicament, especially in the prevention or treatment of gastric and/or duodenal ulcers.

Finally, a subject of the invention is the use of these crystals for the preparation of the magnesium salt of an omeprazole enantiomer in dihdyrate form A, and also to a process for preparing the magnesium salt of an omeprazole enantiomer in dihdyrate form A, characterized in that it comprises a step of controlled dehydration of crystals of the magnesium tetrahydrate salt of an omeprazole enantiomer.

As indicated above, the invention is directed toward proposing processes for achieving the formation of a novel precursor phase that itself gives rise, simply and reproducibly, to the magnesium salt of an omeprazole enantiomer in tetrahydrate form (occasionally referred to hereinbelow for greater simplicity as the "tetrahydrate"), which may itself lead directly to the magnesium salt of the enantiomer in dihydrate form A (occasionally referred to hereinbelow for greater simplicity as the "dihydrate A").

This precursor phase, which has been characterized by X-ray powder diffractometry, thus constitutes a novel route of access not only to the tetrahydrate but also to the dihydrate A, from an omeprazole enantiomer in crystalline or amorphous, optionally hydrated and/or solvated form. The yield for these processes is generally greater than 50%, especially greater than 60%, or even greater than 70%, the latter yield being calculated as the mole ratio of the isolated magnesium salt (tetrahydrate or dihydrate A) to the enantiomer used.

The routes of access to this precursor phase will now be described.

In this description, the term "between" should be understood as including the mentioned limits. In addition, all the 2θ diffraction angle values indicated in this description are given to within 0.2° and should be understood as being measured by X-ray powder diffraction using a copper anticathode tube.

Preparation of the Precursor from an Amorphous Compound

In a first embodiment of the invention, the abovementioned precursor phase is obtained from a magnesium salt of an omeprazole enantiomer in amorphous form.

The magnesium salt of this enantiomer may especially be prepared according to a process comprising:
a) the reaction of an optionally solvated alkali metal salt of said enantiomer with an aqueous solution of magnesium salt free of organic solvent, to obtain a precipitate,
b) the filtration of said precipitate,
c) optionally, the reslurrying of the residue obtained from step (b) in water, followed by filtration,
d) optionally, the drying of the suspension thus obtained.

The alkali metal salt of the enantiomer used in step (a) is advantageously obtained according to a preferential crystallization process comprising: (a1) the transformation of racemic omeprazole into its potassium salt in solvate form, by addition of an excess of mineral base (such as potassium hydroxide) and of a solvent (such as ethanol and/or ethylene glycol), to obtain a conglomerate, (a2) the preparation of a mixture of crystals of said conglomerate, of a first omeprazole enantiomer and of a solvent, (a3) the cooling of the mixture according to certain temperature kinetics, and with increasing stirring, to promote the growth of said enantiomer while avoiding nucleation of the other enantiomer, and (a4) the recovery of the crystals of the first enantiomer. The conglomerate is then added in equal mass to the harvest to the mother liquors, to obtain a two-phase mixture, from which the second enantiomer is in turn crystallized by cooling. This process, known as AS3PC (auto-seeded programmed polythermic preferential crystallization), is described in patent application FR 2 920 428, the teaching of which is incorporated herein by reference.

Preferably, the alkali metal salt of said enantiomer is the potassium salt of (S) omeprazole optionally solvated with ethanol or ethylene glycol. More preferentially, it is the potassium salt of (S) omeprazole solvated with ethanol.

This alkali metal salt is advantageously dissolved in water (generally in the absence of any other solvent or salt), for example at a rate of from 0.1 to 0.5 g/ml, or even from 0.2 to 0.3 g/ml, and is then reacted with an aqueous solution of magnesium salt free of organic solvent, to obtain a precipitate. The magnesium concentration of the aqueous solution may range, for example, from 0.05 to 0.5 g/ml and especially from 0.1 to 0.2 g/ml. It is moreover preferred to use from 0.1 to 1.5 equivalents, more preferentially from 0.5 to 1 equivalent and better still from 0.51 to 0.55 equivalent (molar) of magnesium salt relative to the alkali metal salt of the omeprazole enantiomer.

Examples of magnesium salts that may be used are magnesium acetate, chloride, bromide and sulfate. It is preferred in this step for the solution of the magnesium salt to be added to the solution of the salt of the omeprazole enantiomer, rather than the inverse.

In addition, the reaction is generally performed with stirring, for a duration of 30 seconds to 30 minutes, at a temperature ranging from 0 to 30° C., preferably from 5 to 20° C. and better still at about 10° C.

The compound obtained may be reslurried in water, in particular if it is desired to reduce the content of residual potassium it contains, so that it is less than 1000 ppm and preferably less than or equal to 500 ppm (as measured by flame emission spectrometry). After optional drying under mild conditions, a magnesium salt of the omeprazole enantiomer in amorphous form is obtained.

As a variant, this amorphous salt may be prepared from a magnesium salt of an omeprazole enantiomer in the form of any hydrate, according to a process comprising the steps of: (a) dissolution of said salt in a suitable solvent, (b) filtration under conditions allowing the removal of the crystallization seeds, for example on a 0.23 μm membrane, (c) rapid evaporation or lyophilization in order to obtain a precipitate containing the salt in amorphous form.

Other processes for preparing a magnesium salt of an omeprazole enantiomer in amorphous form are described in document WO 2006/096 709 and may be performed by a person skilled in the art. They comprise the rapid elimination of a solvent (in particular by rapid evaporation) from a solution containing a magnesium salt of an omeprazole enantiomer. This salt may especially be obtained by reacting magnesium in a solvent, such as methanol, with a chlorinated hydrocarbon, such as dichloromethane, to obtain a magnesium alkoxide, which is then reacted with the omeprazole enantiomer.

As a variant, the magnesium salt of the enantiomer in amorphous form may be obtained by atomization of an alcoholic solution of a magnesium salt of said enantiomer in the form of any of its hydrates.

The magnesium salt of the omeprazole enantiomer in amorphous form may be converted into the desired precursor phase according to a process comprising a first step of reslurrying the amorphous compound in a solvent/water mixture, with the proviso of selecting a nonalcoholic polar organic solvent, and of complying with a correct volume proportion of solvent relative to water. The solvent is water-miscible, i.e. at least partially miscible with water and preferably miscible with water in all proportions. This solvent is preferably a ketone such as acetone. As a variant, however, it is possible to use acetonitrile, THF, methyl ethyl ketone or mixtures, in all proportions, of these solvents with each other and/or with acetone.

It has in fact been demonstrated that at a given temperature, the use of an excessively high proportion of water may lead to a salt of an omeprazole enantiomer in trihydrate form, even by performing the subsequent filtration rapidly. Conversely, an excessively high proportion of solvent has a negative impact on the yield, and also on the purity of the dihydrate form A that may be subsequently obtained. The volume proportion of acetone to water may be adjusted between 95/5 and 30/70 by a person skilled in the art, as a function of the working temperature and of the mass ratio of solute (amorphous salt) to the solvent mixture (water and acetone). It is preferred for the volume ratio of acetone to water to be between 75/25 and 40/60, more preferentially between 70/30 and 50/50, in particular when the reslurrying step is performed at room temperature (23° C.). To calculate the volume ratio of solvent to water, the amount of water possibly combined with the amorphous salt should be taken into account, in the case where said salt has not been subjected to a drying step. In any case, it is preferred not to use in this step other solvents or salts than those mentioned above.

The reslurrying step is generally performed with stirring. The stirring time may be between 30 minutes and 15 hours, for example between 1 hour and 12 hours, and in particular between 4 hours and 12 hours. This time may vary as a function of the process parameters (solvent/water volume ratio and working temperature) and of the desired characteristics for the process (especially its production efficiency) and/or the product (in particular its crystallinity).

The temperature at which the reslurrying is performed is generally maintained between −10 and 25° C., preferably between 0 and 15° C. and more preferentially at about 10° C. It has been observed that a lower temperature makes it possible to reduce the acetone/water ratio and thus to increase the yield of tetrahydrate.

This reslurrying step leads to the precursor phase described previously.

Preparation of the Precursor from an Alkali Metal Salt of the Enantiomer

In a second embodiment of the invention, the desired precursor phase may also be obtained from an optionally solvated alkali metal salt of the corresponding omeprazole enantiomer, by reversing the steps of cation exchange and of reslurrying described previously.

The first step of this process comprises the dissolution, in a solvent/water mixture, of said optionally solvated alkali metal salt of the omeprazole enantiomer. The nature of the solvent and the operating conditions of this step may be chosen and may vary to the same extent as in the first embodiment of the invention. However, in this embodiment, it is preferred for the volume ratio of the solvent to water to be between 90/10 and 50/50, for example between 80/20 and 60/40. Moreover, it is preferred to use from 3 to 10 liters of solvent mixture and advantageously from 5 to 7 liters of solvent mixture per kilogram of alkali metal salt used. In any case, it is preferred not to use in this step solvents or salts other than those mentioned above.

In the second step of the process according to the second embodiment of the invention, the solution of the alkali metal salt described above is mixed with an aqueous solution of a magnesium salt free of organic solvent, to form a suspension containing the desired precursor phase. It is preferred in this step for the magnesium salt to be introduced into the solution of alkali metal salt, although the reverse may also be envisioned.

In this case also, the nature and amount of magnesium salt, and the process parameters of this step, may be identical to those described previously with reference to the first embodiment of the invention. It is preferred, however, for the time of reaction between the alkali metal salt and the magnesium salt to be between 30 seconds and 4 hours, for example between 2 and 3 hours, limits inclusive. It is then possible to keep the suspension obtained stirring for a few hours, for example up to 4 hours.

In a third embodiment of the invention, the desired precursor phase may also be obtained from a magnesium salt of an omeprazole enantiomer. This enantiomer may be in any amorphous or crystalline form, optionally in hydrate form (dihydrate A or B, trihydrate, etc.) or solvate form.

The first step of this process consists of reslurrying of the magnesium salt of the enantiomer in at least one water-miscible organic solvent (i.e. a polar organic solvent that is at least partially miscible with water and preferably miscible with water in all proportions), to the exclusion of any other solvent. Examples of such solvents include acetone, THF, methyl ethyl ketone, and mixtures thereof. This step simultaneously allows dissolution of said salt and crystallization of a product in the form of an efflorescent phase. When the solvent is acetone, this phase is characterized in that its X-ray diffractogram has the following characteristic peaks:

| d (Angströms) | 2-Theta (°) | Intensity |
|---|---|---|
| 15.27 | 5.78 | very strong |
| 12.41 | 7.12 | weak |
| 8.52 | 10.37 | weak |
| 7.61 | 11.61 | weak |
| 6.79 | 13.03 | very weak |
| 5.10 | 17.38 | medium |

The temperature at which the reslurrying is performed is generally maintained between −10 and 30° C., preferably between 15 and 25° C., and more preferentially at room temperature. It has been observed that a lower temperature reduced the conversion kinetics. Moreover, the weight/volume ratio of the salt of the enantiomer to acetone is generally between 1/7 and 1/20 (g/ml), for example about 1/10 (g/ml).

The principle of the second step of this process consists in converting said product into the precursor phase of the tetrahydrate by addition of water. This step is generally performed at a temperature of between −10 and 30° C., preferably between 0 and 10° C. In addition, the volume ratio of water to organic solvent (preferably acetone) used in the second step is generally between 5/95 and 60/40, for a temperature in the region of 10° C., or even between 3/97 and 70/30 for a temperature close to 0° C.

Preparation and Uses of the Tetrahydrate

It was observed that the precursor phase obtained according to one of the abovementioned embodiments of the invention gave rise, surprisingly, by simple filtration of the medium containing it, to the magnesium salt of the omeprazole enantiomer in tetrahydrate form.

This step of filtration of the suspension may be performed using an open filter, a closed filter, a drying filter or a suction filter. It is preferred for it to be performed on a funnel sinter or by centrifugation. The filtration step may optionally be followed by rinsing and drying of the product or "cake" obtained, under mild conditions.

The rinsing may be performed with water or with a polar organic solvent such as acetone. The choice of solvent has an influence on the yield for the process and the crystallinity of the product obtained. This crystallinity is improved when acetone is used, at the expense of the yield, which is better when water is used. As a variant, it is possible to rinse the tetrahydrate successively with water and then with acetone or with a water/acetone mixture. In particular, it has been demonstrated that final rinsing with acetone makes it possible subsequently to obtain the dihydrate A in greater purity. The rinsing may be performed by percolation of these solvents through the tetrahydrate, or by rapid slurrying of the tetrahydrate in these solvents, followed by a final filtration step.

The drying step is itself generally performed under mild conditions (temperature from 20 to 25° C., atmospheric pressure, under a stream of non-dry air) to avoid degrading the tetrahydrate, which constitutes a metastable phase.

The tetrahydrate obtained is not, however, unstable under conditions of ambient temperature, pressure and relative humidity. It may be characterized by its X-ray powder diffractogram, as indicated in Example 3 below.

This compound may be used as a medicament, especially in the prevention or treatment of gastric and/or duodenal ulcers. In this perspective, it may be conveyed in any type of solid composition, for example in the form of gel capsules, tablets, soft capsules, granules or powder to be diluted extemporaneously, to make a medicament suitable for oral administration. These compositions may comprise pharmaceutically acceptable excipients, which a person skilled in the art can easily select as a function of the adopted galenical form, and optionally one or more other therapeutic active agents. The amount of tetrahydrate included in these compositions depends on the administered daily dose, which may itself range between 5 and 300 mg, for example, and also on the number of envisaged daily doses.

As a variant, it may be used for the preparation of the magnesium salt of an omeprazole enantiomer in dihydrate form A.

The present invention thus also relates to these uses and in particular to a process for preparing the magnesium salt of an omeprazole enantiomer in dihydrate form A, characterized in that it comprises a step of controlled dehydration of crystals of the magnesium tetrahydrate salt of an omeprazole enantiomer that may be obtained as described previously.

This step of controlled dehydration may include drying:
at a temperature of between 40 and 65° C., under a pressure of 1 bar or advantageously under vacuum, optionally at 0% relative humidity, or
at a temperature of between 20 and 40° C., for example at room temperature (23° C.), under vacuum and/or under 0% relative humidity (for example under $P_2O_5$ or under a stream of dry nitrogen).

To obtain a purer product, it is preferred according to the invention for the product to be dried under vacuum (between 1 and 100 millibar, preferentially between 20 and 80 millibar and better still between 40 and 60 millibar), at a temperature of between 20 and 40° C. (advantageously in the region of 30° C.) for a time ranging from 10 hours to 3 days, optionally in the presence of a gentle stream of nitrogen.

BRIEF DESCRIPTIONS OF THE DRAWINGS

Other advantages and characteristics of the invention will emerge from the examples that follow and in which reference will be made to the attached figures, in which.

DETAILED DESCRIPTION OF THE INVENTION

Examples

Analytical Methods Used

Determination of the Enantiomeric Excess (% ee)

The enantiomeric excesses are determined by chiral HPLC chromatography using a ChiralPAK AD column (dimensions 250 mm×4.6 mm). The experimental conditions are:
Solvent: 100% absolute ethanol
Flow rate: 1 ml·min$^{-1}$
Detector: λ=302 nm
Injection: 20 µL
Concentration: about 0.4 g·l$^{-1}$ in ethanol.
Analyses by X-Ray Powder Diffraction The X-ray powder diffraction (XRPD) analyses were performed using a Bruker D8 diffractometer equipped with a Lynx Eye detector under the following conditions:
copper anticathode, voltage 40 kV, current 40 mA
ambient temperature
measuring range: 3° to 30°
incrementation between each measurement: 0.04°
measuring time per step: 1.5 seconds.
Calorimetric and Thermogravimetric Measurements The TGA-DSC analyses were performed using a Netzsch STA 449C TGA-DSC machine. The measurements are performed in an aluminum crucible, between 0° and 200° C. with a heating rate of 2° C.·min$^{-1}$ while flushing with 60 ml·min$^{-1}$ of helium.

Example 1

Preparation of the Magnesium Salt of Amorphous Esomeprazole

The potassium salt of esomeprazole solvated with ethanol, obtained according to the process described in patent WO 2009/027 614, is dissolved (10 g) in water (40 ml). An aqueous magnesium acetate solution (10 ml, 37 g·l$^{-1}$ of Mg$^{2+}$) is added to the preceding solution dropwise, stirring. The white precipitate obtained is stirred for 30 minutes and then filtered on a No. 3 sinter. The white precipitate thus recovered is reslurried in 40 mL of water for 30 minutes, filtered on a No. 3 sinter and then dried. This white precipitate is a magnesium salt of amorphous esomeprazole.

Figure 1:
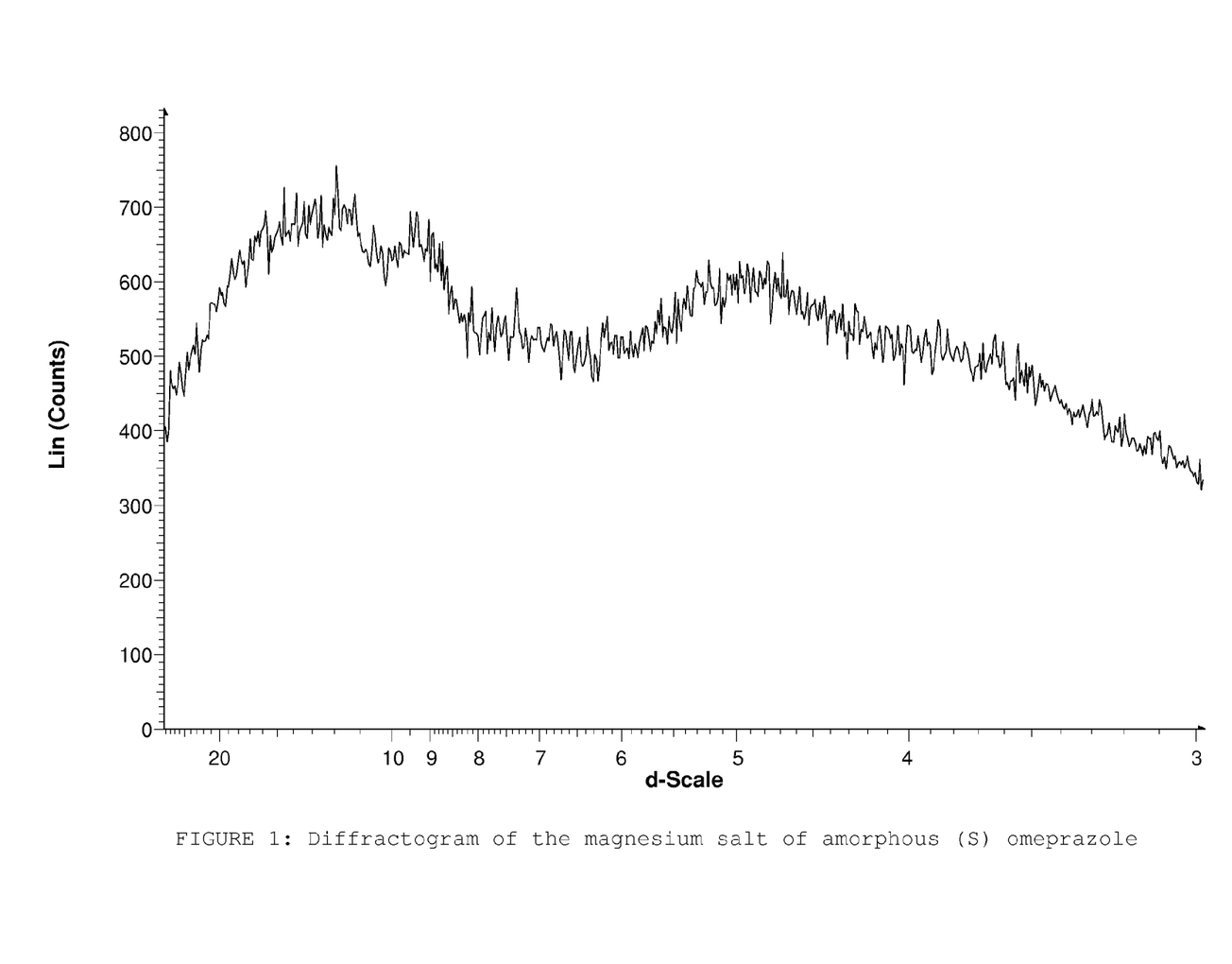
FIG. 1 shows the diffractogram of the magnesium salt of amorphous esomeprazole.

The diffractogram (XRPD) of this compound is shown in FIG. 1.

Example 2

Preparation of the Magnesium Salt of Amorphous (S) Omeprazole

The potassium salt of (S) omeprazole solvated with ethanol, obtained according to the process described in patent WO 2009/027 614, is dissolved (10 g) in water (40 ml). An aqueous magnesium acetate solution (20 ml, 19 g·l$^{-1}$ of Mg$^{2+}$) is added to the preceding solution dropwise, with stirring. The white precipitate obtained is stirred for 20 minutes and then filtered through a No. 3 sinter and dried. This white precipitate is a magnesium salt of amorphous (S) omeprazole.

Example 3

Preparation of the Magnesium Salt of (S) Omeprazole Tetrahydrate (Route 1)

The magnesium salt of amorphous (S) omeprazole prepared in Example 1 is reslurried in an acetone (45 ml)/water (15 ml) mixture. The suspension is stirred for two hours, filtered and then dried (at ambient temperature and pressure).

The white solid obtained is the magnesium tetrahydrate salt of (S) omeprazole. This compound was obtained in a yield of 62%.

Figure 2:
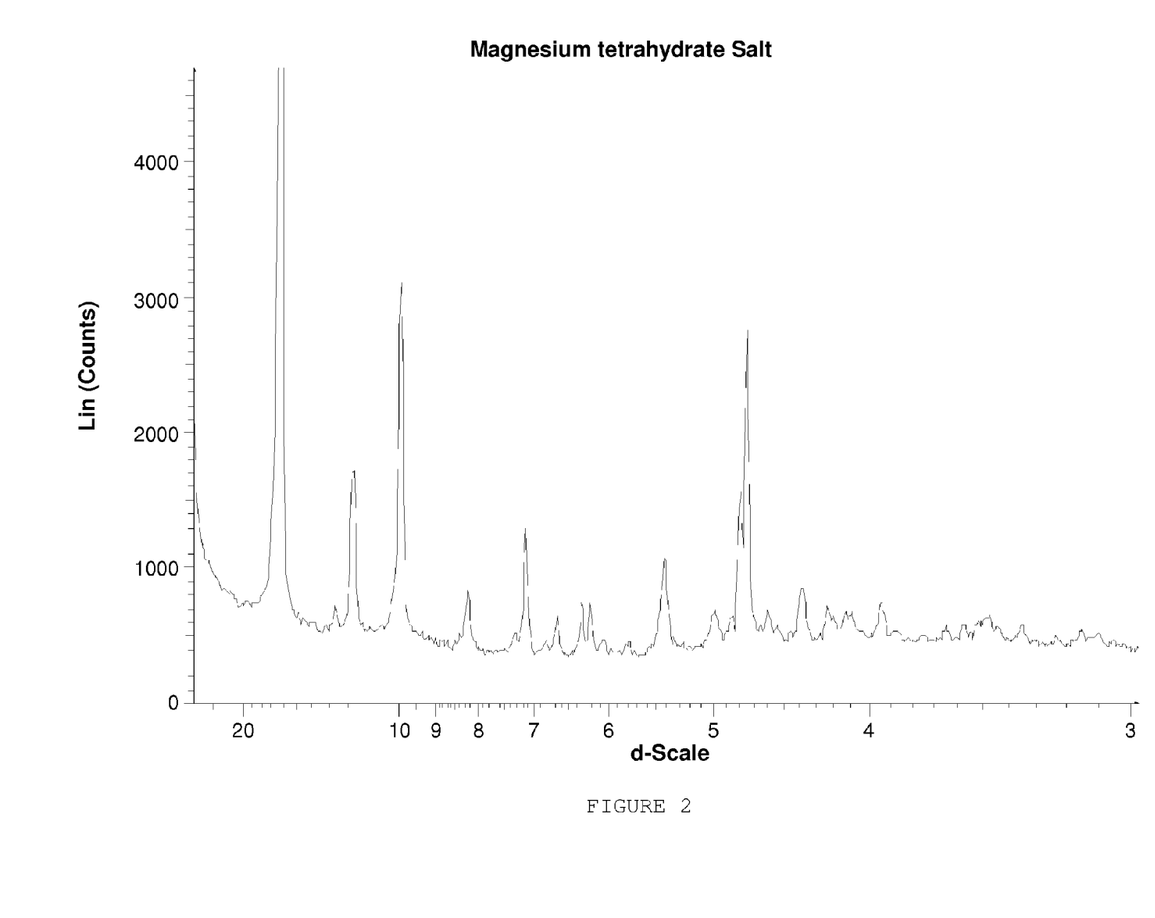
FIG. 2 shows the diffractogram of the magnesium tetrahydrate salt of esomeprazole.
Figure 3:
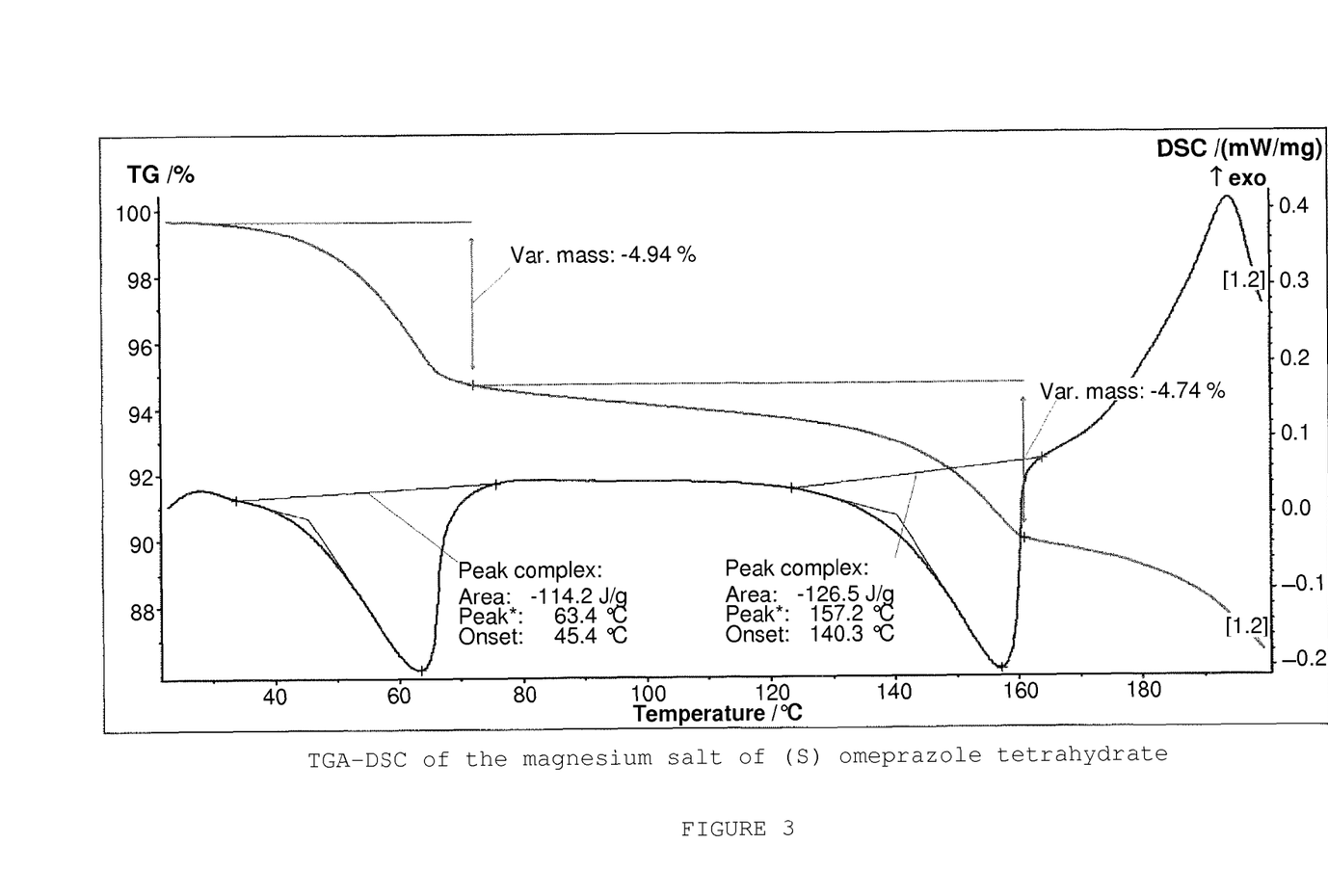
FIG. 3 shows the TGA-DSC of the magnesium tetrahydrate salt of esomeprazole.

The diffractogram (XRPD) of this compound is shown in FIG. 2 and its TGA-DSC is shown in FIG. 3.

Table I below shows the position and relative intensity of the characteristic peaks of the magnesium tetrahydrate salt of enantiomerically pure esomeprazole (i.e. having an e.e. purity>99%).

TABLE I

Magnesium salt of esomeprazole tetrahydrate

| Angle 2-Theta (2θ) | d (Angströms) | Intensity I/Io % |
|---|---|---|
| 5.37 | 16.46 | 100 |
| 7.36 | 11.00 | 11.4 |
| 8.76 | 10.09 | 26.6 |
| 10.63 | 8.31 | 6.6 |
| 12.26 | 7.21 | 7.1 |
| 16.21 | 5.46 | 10.4 |
| 17.61 | 5.03 | 6.9 |
| 18.28 | 4.848 | 13 |
| 18.50 | 4.791 | 21.9 |

Example 4

Preparation of the Magnesium Tetrahydrate Salt of (S) Omeprazole (Route 1)

The white solid obtained in Example 2 is successively reslurried in 120 ml of an acetone/water mixture (75/25 V/V %) for 2 hours and then in 60 ml of an acetone/water mixture (85/15 V/V %) for 1 hour. After filtering and drying, the magnesium tetrahydrate salt of (S) omeprazole is recovered in a yield of 55%.

Example 5

Preparation of the Magnesium Tetrahydrate Salt of (S) Omeprazole (Route 1)

The white solid obtained in Example 2 is successively reslurried in 120 ml of an acetone/water mixture (75/25 V/V %) for 2 hours and then in 60 ml of an acetone/water mixture (85/15 V/V %) for 1 hour. After filtering and drying, the magnesium tetrahydrate salt of (S) omeprazole is recovered in a yield of 52%.

Example 6

Preparation of the Magnesium Tetrahydrate Salt of (S) Omeprazole (Route 1)

This example illustrates one preparation method not including the step of drying the amorphous intermediate product formed.

Figure 4:
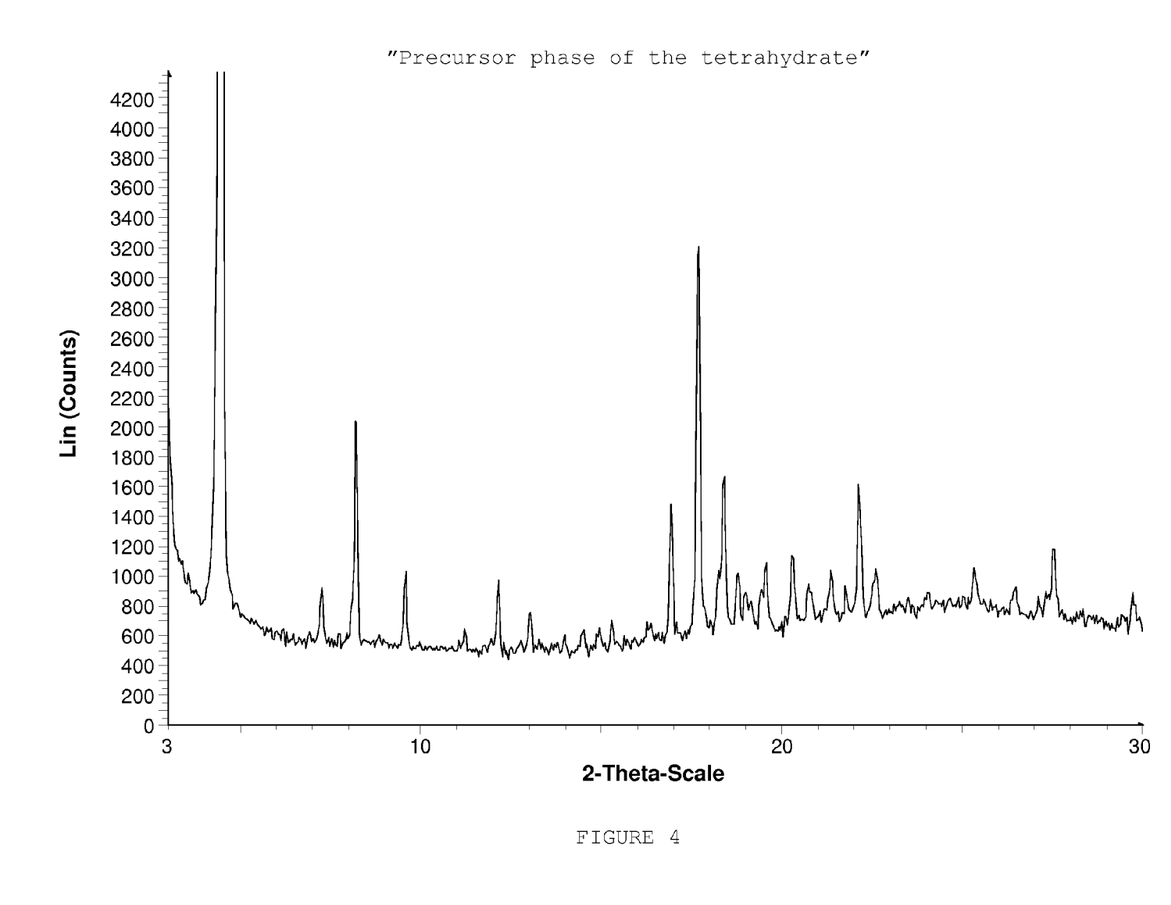
FIG. 4 shows the diffractogram of the precursor phase of the tetrahydrate.

20 g of the potassium salt of esomeprazole solvated with ethanol, obtained according to the process described in patent WO 2009/027 614, were dissolved in 80 ml of water, at room temperature. 4.96 g of magnesium acetate tetrahydrate in 10 ml of demineralized water were added to this solution, with stirring, followed by a further 30 ml of water. After stirring for a few minutes, the medium was filtered by suction on a sinter. The cake obtained was reslurried in an acetone/water mixture containing 55 ml of acetone and 5 ml of water, i.e. a 50/50% by volume mixture, taking into account the amount of water included in the cake (40 ml). Stirring was continued for 1 hour, after which the precursor phase of the tetrahydrate in the suspension was revealed. This was characterized by XRD. Its diffractogram is shown in the attached FIG. 4.

The cake was then filtered on a sinter and washed with 20 ml of water. The magnesium tetrahydrate salt of (S) omeprazole was thus isolated.

Example 7

Preparation of the Magnesium Tetrahydrate Salt of (S) Omeprazole (Route 2)

312.5 g of the potassium salt of esomeprazole solvated with ethanol, obtained according to the process described in patent WO 2009/027 614, were dissolved in 625 ml of water, followed by addition of 1250 ml of acetone. The medium was then stirred and cooled to 10° C., and 71.85 g of magnesium acetate tetrahydrate in 625 ml of demineralized water were introduced over a period of three hours. After stirring overnight at 10° C., the presence of the precursor phase in the medium was revealed.

This medium was then filtered by suction on a sinter, and the cake was then washed twice with demineralized water (2×625 ml), and then twice with acetone (2×625 ml). The isolated and dried product corresponded to the magnesium salt of esomeprazole tetrahydrate.

Example 8

Preparation of the Magnesium Tetrahydrate Salt of (S) Omeprazole (Route 3)

1 g of magnesium trihydrate salt was reslurried overnight in 10 mL of acetone at room temperature. The suspension was then cooled to 10° C. and 10 mL of water were then added. After stirring for 3 hours at 10° C., the medium was filtered on a sinter and rinsed with 20 mL of acetone. The product, corresponding to the magnesium tetrahydrate salt, was isolated in a yield of 77%.

Example 9

Preparation of the Magnesium Tetrahydrate Salt of (S) Omeprazole (Route 3)

1 g of magnesium trihydrate salt was reslurried for one hour in 10 mL of acetone at room temperature. The suspension was then cooled to 10° C., and 0.8 mL of water was then added. After stirring for 3 hours at 10° C., the medium was filtered on a sinter and rinsed with 20 mL of acetone. The product, corresponding to the magnesium tetrahydrate salt, was isolated in a yield of 84%.

Example (Comparative) 10

Potassium salt of esomeprazole (7 g) is dissolved in water with an excess of potassium hydroxide (0.8 g, i.e. 0.2 molar equivalent). Excess magnesium chloride is added (22.8 g, i.e. about 5 molar equivalents), predissolved in a water/acetone solution (50 ml/100 ml). This solution is added dropwise with stirring. The solid is recovered by filtration on a Büchner funnel, and then rinsed thoroughly with distilled water.

This solid does not correspond to the magnesium tetrahydrate salt of (S) omeprazole. It is probable that it is the corresponding trihydrate, which is more stable.

Example 11

Preparation of the Magnesium Salt of (S) Omeprazole Dihydrate Form A

The tetrahydrate obtained in Example 2 is dried under 0% relative humidity, at 40° C. The solid recovered is (S) omeprazole dihydrate form A in a yield of greater than 99%.

Figure 5:
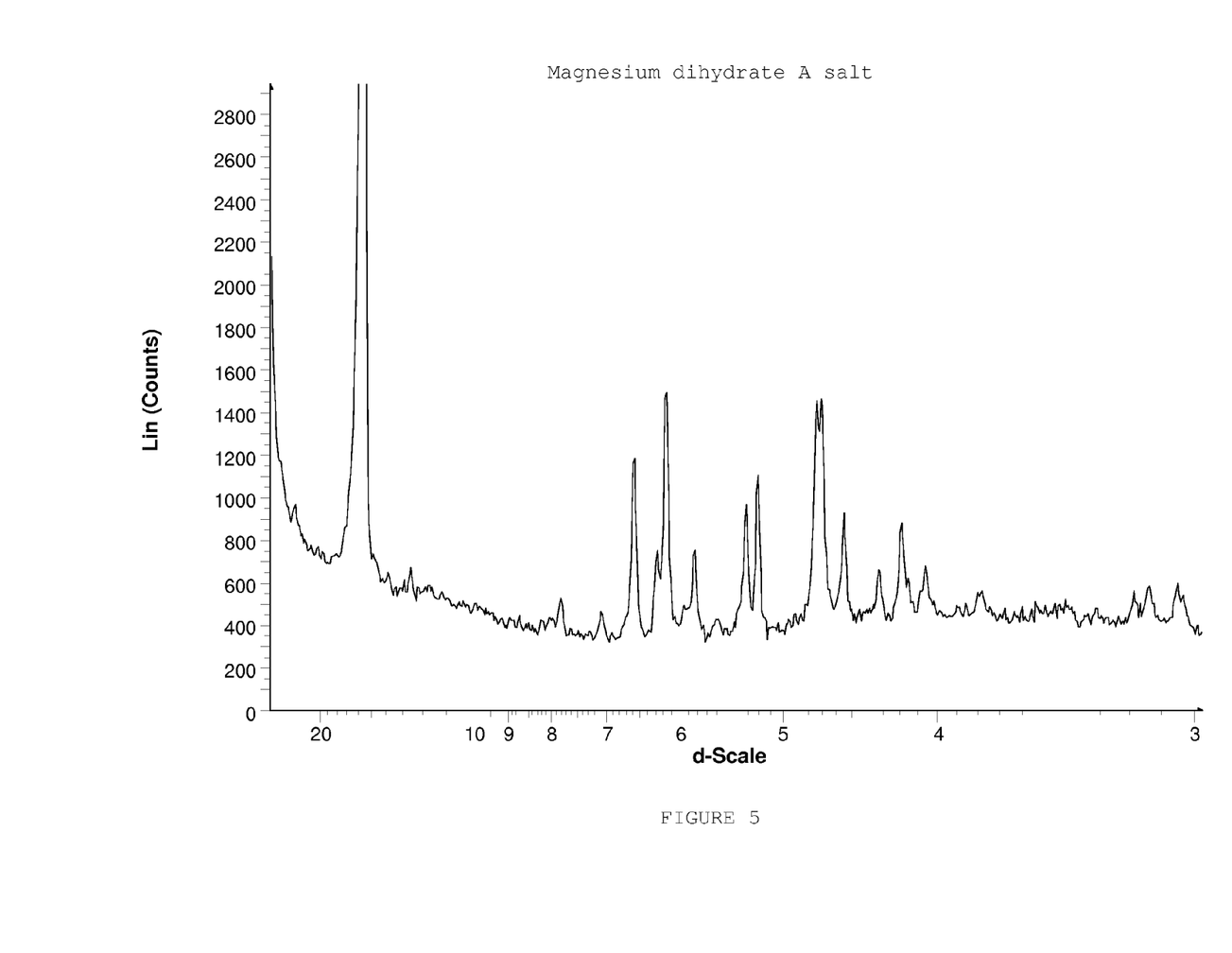
FIG. 5 shows the diffractogram of the dihydrate form A of the magnesium salt of esomeprazole.
Figure 6:
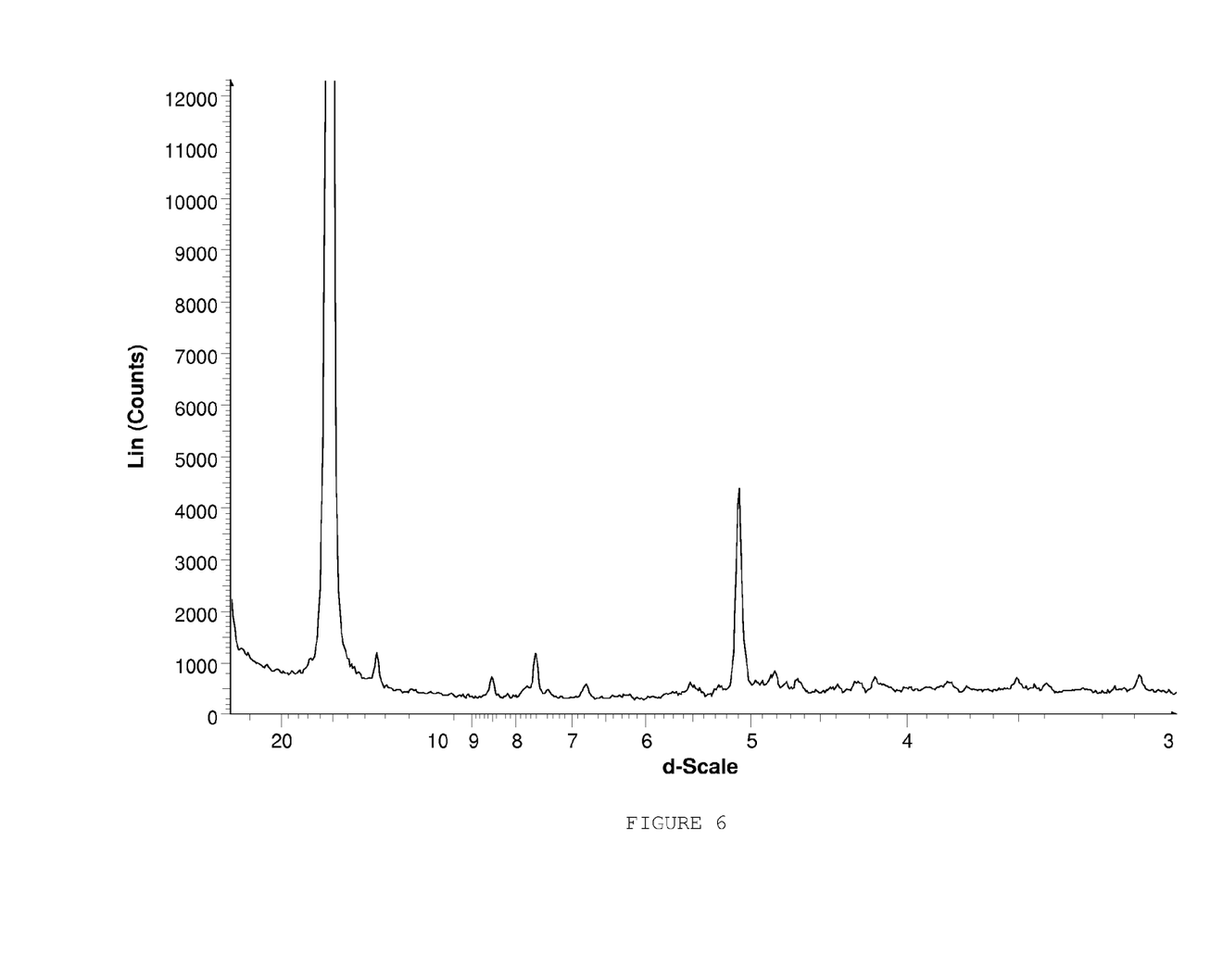
FIG. 6 shows the diffractogram of the efflorescent phase leading to the precursor phase of the tetrahydrate.

The X-ray powder diffractogram (XRPD) of this phase is shown in FIG. 5.

Table II below moreover shows the position and relative intensity of the characteristic peaks for the dihydrate form A of enantiomerically pure magnesium salt of esomeprazole (i.e. having an e.e. purity>99%).

TABLE II

| Magnesium salt of esomeprazole dihydrate form A | | |
|---|---|---|
| Angle 2-Theta (2θ) | d (Angströms) | Intensity I/Io % |
| 5.52 | 16.0 | 95.3 |
| 13.31 | 6.65 | 52.9 |
| 13.92 | 6.36 | 38.4 |
| 14.26 | 6.21 | 85.6 |
| 15.08 | 5.872 | 46.7 |
| 16.53 | 5.359 | 46.4 |
| 16.85 | 5.258 | 35.8 |
| 18.69 | 4.744 | 100 |
| 19.38 | 4.577 | 61.8 |
| 20.37 | 4.357 | 42 |
| 21.06 | 4.214 | 63.7 |
| 21.73 | 4.086 | 41.4 |
| 23.33 | 3.810 | 29.6 |
| 27.85 | 3.201 | 33.9 |
| 28.25 | 3.157 | 34.3 |
| 29.13 | 3.063 | 33.6 |

Example 12

Preparation of the Magnesium Salt of (S) Omeprazole Dihydrate Form A

The tetrahydrate obtained in Example 2 is dried at 60° C. (preferably under 0% relative humidity). The solid recovered is (S) omeprazole dihydrate form A in a yield of greater than 99%.

Example 13

Preparation of the Magnesium Salt of (S) Omeprazole Dihydrate Form A

The tetrahydrate obtained in Example 2 is dried under 0% relative humidity, at 20° C. and under a pressure of 100 mbar. The solid recovered is (S) omeprazole dihydrate form A, in a yield of greater than 99%.

Example 14

Preparation of the Magnesium Salt of (S) Omeprazole Dihydrate Form A

The product obtained in Example 7 was dried under vacuum at 30° C., while flushing with nitrogen. The dihydrate A was obtained in a yield of 80.9% relative to the alkali metal salt of the omeprazole enantiomer used during Example 7.

Example (Comparative) 15

The magnesium salt of amorphous (S) omeprazole (0.5 g), prepared in Example 1, is reslurried in acetone (10 mL) for 2 hours, filtered off and then dried (at ambient temperature and pressure). The white solid obtained is a dihydrate form B of the magnesium salt of (S) omeprazole, as indicated by the diffractogram (XRPD) of this phase.

The invention claimed is:

1. A process for preparing the magnesium salt of an omeprazole enantiomer in dihydrate form A, comprising:
a step of controlled dehydration by drying at:
   (i) a temperature of between 40 and 65° C., under a pressure of 1 bar or under vacuum, or
   (ii) a temperature of between 20 and 40° C., under vacuum and/or at 0% relative humidity,
of crystals of a magnesium tetrahydrate salt of an omeprazole enantiomer, said crystals being obtained by filtration and then drying of a suspension containing a precursor phase of said magnesium tetrahydrate salt, wherein the precursor has an X-ray diffractogram of the following characteristic peaks:

| d (Ångströms) | 2-Theta (°) | Relative intensity (%) |
|---|---|---|
| 19.80 | 4.45 | very strong |
| 12.17 | 7.25 | weak |
| 10.78 | 8.19 | medium |
| 9.26 | 9.53 | weak |
| 7.28 | 12.14 | weak |
| 6.79 | 13.03 | weak |
| 5.22 | 16.95 | weak |
| 5.01 | 17.67 | medium |
| 4.821 | 18.38 | weak |
| 4.009 | 22.15 | weak. |

2. The process according to claim 1, wherein the drying is:
   (i) at a temperature of between 40 and 65° C., under a pressure of 1 bar or under vacuum, is at 0% relative humidity, or
   (ii) at room temperature, under vacuum and/or at 0% relative humidity.

3. The process according to claim 1, wherein the precursor phase is prepared by reslurrying of the magnesium salt of said enantiomer in amorphous form in a solvent/water mixture, said solvent being a water-miscible nonalcoholic organic solvent and the volume ratio of the solvent to water being between 95/5 and 30/70.

4. The process according to claim 3, wherein the magnesium salt of said enantiomer in amorphous form used for preparing the precursor phase is obtained according to a process comprising the following steps:

a) reacting an optionally solvated alkali metal salt of said omeprazole enantiomer with an aqueous solution of magnesium salt free of organic solvent, to obtain a precipitate,
b) filtering said precipitate,
c) optionally, reslurrying the residue obtained from step (b) in water, followed by filtering,
d) optionally, drying the suspension obtained.

5. The process according to claim 3, wherein the organic solvent is selected from the group consisting of: ketones, acetonitrile, THF, and mixtures thereof.

6. The process according to claim 4, wherein the optionally solvated alkali metal salt of said omeprazole enantiomer used for preparing the magnesium salt of said enantiomer in amorphous form is the potassium salt of (S) omeprazole optionally solvated with ethanol or ethylene glycol.

7. The process according to claim 4, wherein the magnesium salt used for preparing the magnesium salt of said enantiomer in amorphous form is selected from the group consisting of magnesium acetate, sulfate, bromide and chloride.

8. The process according to claim 1, wherein the precursor phase is prepared by a process which comprises:
dissolving an optionally solvated alkali metal salt of said omeprazole enantiomer in a solvent/water mixture, said solvent being a water-miscible nonalcoholic organic solvent and the volume ratio of the solvent to water being between 90/10 and 50/50, and
mixing of said solution with an aqueous solution of a magnesium salt free of organic solvent, to form a suspension.

9. The process of according to claim 8, wherein the organic solvent is selected from the group consisting of: ketones, acetonitrile, THF, and mixtures thereof.

10. The process of according to claim 8, wherein the optionally solvated alkali melt salt of said omeprazole enantiomer used for preparing the precursor phase is the potassium salt of (S) omeprazole optionally solvated with ethanol or ethylene glycol.

11. The process according to claim 8, wherein the magnesium salt used for preparing the precursor phase is selected from the group consisting of magnesium acetate, sulfate, bromide and chloride.

12. The process according to claim 1, wherein the precursor phase is prepared by a process which comprises:
reslurrying in at least one water-miscible nonalcoholic organic solvent, to the exclusion of any other solvent, of a magnesium salt of an amorphous or crystalline, optionally hydrated or solvated, omeprazole enantiomer, and adding water to the product thus obtained.

13. The process according to claim 12, wherein the organic solvent is selected from the group consisting of: ketones, acetonitrile, THF, and mixtures thereof.

* * * * *